(12) United States Patent
Clayman et al.

(10) Patent No.: US 11,576,744 B2
(45) Date of Patent: Feb. 14, 2023

(54) THERMOSENSITIVE BIO-ADHESIVE HYDROGEL FOR REMOVAL OF URETERAL AND RENAL STONES

(71) Applicants: UROGEN PHARMA LTD., Ra'anana (IL); The Regents of the University of California, Oakland, CA (US)

(72) Inventors: Ralph V. Clayman, Irvine, CA (US); Pengbo Jiang, Irvine, CA (US); Mark Schoenberg, Pikesville, MD (US); Omer Tsipori, Sha'ar Efraim (IL)

(73) Assignees: THE REGENTS OF THE UNIVERSITY OF CALIFORNIA, Oakland, CA (US); UROGEN PHARMA LTD., Ra'anana (IL)

( * ) Notice: Subject to any disclaimer, the term of this patent is extended or adjusted under 35 U.S.C. 154(b) by 0 days.

(21) Appl. No.: 17/703,238

(22) Filed: Mar. 24, 2022

(65) Prior Publication Data
US 2022/0304766 A1   Sep. 29, 2022

Related U.S. Application Data

(60) Provisional application No. 63/165,744, filed on Mar. 25, 2021.

(51) Int. Cl.
| A61B 90/00 | (2016.01) |
| A61B 18/26 | (2006.01) |
| A61L 24/00 | (2006.01) |
| A61L 24/08 | (2006.01) |
| A61K 31/722 | (2006.01) |
| A61B 17/22 | (2006.01) |

(52) U.S. Cl.
CPC .............. *A61B 90/04* (2016.02); *A61B 18/26* (2013.01); *A61K 31/722* (2013.01); *A61L 24/0031* (2013.01); *A61L 24/08* (2013.01); *A61B 17/22004* (2013.01); *A61B 2017/22082* (2013.01); *A61B 2090/049* (2016.02); *A61B 2090/0472* (2016.02)

(58) Field of Classification Search
CPC .................... A61B 90/04; A61B 18/26; A61B 2017/22082; A61B 2090/0472; A61B 2090/049; A61B 17/22004; A61L 24/0031; A61L 24/08; A61K 31/722
See application file for complete search history.

(56) References Cited

U.S. PATENT DOCUMENTS

| 8,361,455 B2 * | 1/2013 | McDougal | A61K 47/36 424/78.37 |
| 8,372,037 B2 | 2/2013 | Sahatjian | |
| 8,409,218 B2 * | 4/2013 | Schwarz | A61B 17/12186 604/93.01 |
| 8,998,928 B2 | 4/2015 | Schwarz | |
| 9,925,311 B2 | 3/2018 | Grunwald | |
| 2012/0253333 A1 * | 10/2012 | Garden | A61B 18/203 606/9 |
| 2019/0083527 A1 * | 3/2019 | Beal | A61K 31/4172 |

FOREIGN PATENT DOCUMENTS

WO    2005/037062    4/2005

* cited by examiner

*Primary Examiner* — Shirley V Gembeh
(74) *Attorney, Agent, or Firm* — JMB Davis Ben-David

(57) ABSTRACT

Provided herein are methods for treating nephrolithiasis and protecting the urothelium and inner lining of the kidney from thermal damage during lithotripsy by use of a thermosensitive bio-adhesive hydrogel. The described method dramatically improved the efficiency and effectiveness of stone clearance compared to conventional techniques while providing protection to the urothelium from potentially damaging temperature spikes.

20 Claims, No Drawings

THERMOSENSITIVE BIO-ADHESIVE HYDROGEL FOR REMOVAL OF URETERAL AND RENAL STONES

CROSS REFERENCE TO RELATED APPLICATIONS

Benefit is claimed to U.S. Provisional Patent Application No. 63/165,744, filed Mar. 25, 2021, the contents of which are incorporated by reference in their entirety.

FIELD

Provided herein are compositions and methods for treatment of nephrolithiasis which provide protection from thermal damage to the urothelium and potential urosepsis from disruption of the inner lining of the kidney during lithotripsy.

BACKGROUND

Nephrolithiasis, commonly known as kidney stones, is a common urological pathology, affecting approximately 9% of adults in the United States. The gold standard outcome for the treatment of stones is stone-free status, defined as elimination of all stone fragments based on a post-operative CT scan. Residual fragments, even those less than 2 mm in size, are associated with stone recurrence. Flexible ureteroscopy serves as a viable first-line therapy for the treatment of stones less than 15 mm; however, after laser lithotripsy, and despite meticulous basketing of stone fragments, 40-45% of patients have stone remnants as the stone baskets are not designed to remove fragments smaller than 2 mm. In addition, there are smaller stone particles (known as "dust" that are commonly <250μ) that tend to congregate in the most dependent portion of the kidney. There is discussion in the literature to eliminate these residual fragments by means of aspiration, or by use of autologous blood to bind fragments together into a clot large enough to be evacuated using a stone basket, or by use of certain gel compositions (Cloutier et al. Urolithiasis. 2014 October; 42(5):441-444; Hein et al. J Urol. 2016; 196(6):1772-1777). However, outside of the autologous clot approach, such methods have not been clinically tested.

The advent of higher-powered lasers for fragmenting renal calculi has resulted in concerns over temperature spikes inside the collecting system of the kidney. Indeed, the superpulse Thulium fiber laser can lead to temperatures within the collecting system well in excess of the 44° C. threshold for tissue injury. To date, there has been no mechanism provided to mitigate this situation other than using a ureteral access sheath during the procedure to promote rapid flow of cooling irrigation fluid; however, the sheath adds to the cost of the procedure and has been associated with splitting of the ureter in upwards of 20% of cases in which it has been deployed (Loftus, CS, Monga, M. et al. JE: 34: 932, 2020).

Although certain poloxamer gel compositions have demonstrated the ability to protect non-targeted tissues from microwave-related thermal damage, use of a poloxamer-based gel to protect tissue directly exposed to high energy lasers used for lithotripsy has not been shown (Moreland et al. Cardiovasc. Intervent. Radiol. 38:722-730(2015); see also Johnson, Int. J. of Hyperthem. 31:551-559 (2015)).

Thus, there remains a pressing need for an effective method for removal of small stone fragments which contemporary flexible stone baskets fail to extract, as well as a method to protect the patient from potential harm from excessive temperatures or renal backflow.

SUMMARY

Provided herein are methods for treatment of a nephrolithiasis in a subject, by administering to the subject a thermosensitive bio-adhesive hydrogel; and providing a lithotripsy procedure to the subject, wherein stone clearance rate is at least 90%, and wherein the thermo-reversible hydrogel comprises chitosan or at least one tri block copolymer having a general formula ABA or BAB copolymer, wherein A is a hydrophilic polymer block and B is a hydrophobic block polymer, thereby treating the nephrolithiasis.

Also described herein are methods for protecting a subject from thermal damage or disruption during lithotripsy, by administering to the subject a thermosensitive bio-adhesive hydrogel; and providing a lithotripsy procedure to the subject, wherein the administration of the thermosensitive bio-adhesive hydrogel protects the subject from urothelium thermal damage associated with the lithotripsy, and wherein the thermo-reversible hydrogel comprises chitosan or at least one tri block copolymer having a general formula ABA or BAB copolymer, wherein A is a hydrophilic polymer block and B is a hydrophobic block polymer, thereby protecting the subject from thermal damage or disruption of the lithotripsy procedure.

Further provided herein are methods for inhibition of nephrolithiasis regrowth in a subject, by administering to the subject a thermosensitive bio-adhesive hydrogel; and providing a lithotripsy procedure to the subject, wherein the administration of the thermosensitive bio-adhesive hydrogel encapsulates the renal stones and prevents displacement of renal stones during the lithotripsy procedure, and wherein the thermo-reversible hydrogel comprises chitosan or at least one tri block copolymer having a general formula ABA or BAB copolymer, wherein A is a hydrophilic polymer block and B is a hydrophobic block polymer, thereby inhibiting renal stone regrowth in a subject.

The foregoing and other objects, features, and advantages will become more apparent from the following detailed description.

DETAILED DESCRIPTION

I. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all molecular weight or molecular mass values are approximate and are provided for description. Although methods and materials similar or equivalent to those described herein can be used in the practice or testing of this disclosure, suitable methods and materials are described below. The term "comprises" means "includes." "Consisting essentially of" indicates a composition, method, or process that includes only those listed features as the active or essential elements, but can include non-active elements in addition. The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Administration: The introduction of a composition into a subject by a chosen route. Administration of an active compound or composition can be by any route known to one of skill in the art, and as appropriate for the compound and the delivery system. For example, the compositions for use in the described methods are typically administered locally, such as through a catheter, to the inside surface of a body cavity, such as the surfaces and cavities for the urothelial system. In particular embodiments, local delivery of the described composition is by intravesical instillation to the target body cavity.

Body cavity: Any fluid-filled space internal to a multicellular organism. In particular embodiments, a body cavity can include other body cavities. For example, the mammalian pelvic cavity includes the bladder, and the thoracic cavity includes the upper gastro-intestinal tract and cavities such as the esophagus. In particular embodiments, a body cavity can be the urinary tract, such as the bladder and/or the pyelocaliceal system and/or the ureters.

Clearance: In the present disclosure the term "clearance" relates to removal of a mineral deposit, such as a renal stone, that may have accumulated in one or more areas in the urinary tract. It may also refer to removal of mineral deposits accumulated in the pancreas, gall bladder, bile ducts, or liver. Clearance is not an absolute value, and is not meant to be interpreted as 100% removal of the mineral deposit, however it may be 100% removal of the deposit. Clearance is understood to be removal of a mineral deposit such that either the mineral deposit is successfully removed intact or fragmented. In particular embodiments, clearance of a kidney stone, or fragment thereof can refer to removal of at least 90%, 91%, 92%, 92.2.%, 93%, 94%, 95%, 96%, 97%, 98% 99%, 99.5%, 99.99% to 100% of the stone or fragment mass. The gold standard for determining an accurate complete clearance rate is via CT scans with 2-3 mm cuts.

Instillation: Instillation can be intraureteral instillation and intrarenal instillation. Installation may also be intravesical instillation, Also known as "intravesical therapy". The term instillation used herein to describe a medical procedure involving the direct/local administration of a drug into the bladder, uretera, or any part of the renal system. Comparable drug administration is possible for other body cavities. In particular embodiments, instillation involves delivery of a drug through a catheter. In particular embodiments of the methods described herein, hydrogel-based compositions, such as reverse thermal (thermoreversible) hydrogels are provided to a subject by instillation.

Lithotripsy: Lithotripsy entails shattering a concretion, such as a mineral deposit, (by light, chemical, or physical energy), and dispersing, collecting, and/or removing the resulting fragments from the original location of the concretion. There are two main categories of lithotripsy: extracorporeal lithotripsy and intracorporeal lithotripsy. Extracorporeal lithotripsy describes a method where the energy needed to break apart a target, such as a kidney stone or fragment thereof, is generated outside the body; while intracorporeal lithotripsy describes a method where the energy needed is generated inside the body via a device delivered through an endoscope.

Nephrolithiasis: A condition involving renal calculi, nephroliths or kidney stones found in one or more areas in the urinary tract of a subject, such as the major calices, minor calices, renal pelvis, and ureter. Renal calculi or kidney stones can spontaneously pass into the ureter resulting in blockage of the ureter with attendant significant health concerns, including pain, bleeding, sepsis, and/or loss of renal function.

Thermal Damage: Standard treatment of nephrolithiasis includes lithotripsy, and in particular embodiments laser-mediated lithotripsy. During the laser-mediated lithotripsy, the target renal stone is hit with continuous firing from a laser, which leads to temperature spikes in the tissue surrounding the target. Such temperature spikes pose a risk of urothelial thermal damage, such as when intra-calyceal temperature rises over 44° C. In a particular embodiment, the compositions and methods described herein are used to protect the urothelium m a subject from such thermal damage. 44° C. is considered the threshold for thermal damage to the urothelium. In particular, and as demonstrated herein, use of the described thermosensitive bio-adhesive hydrogel insulates the urothelium and prevents the intra-calyceal temperature from exceeding 36° C.

Renal Backflow: Renal backflow, which may also be referred to as pyelovenous, pyelosinus or pyelolymphatic in nature, is a condition in which there is an abnormal flow of urine from the kidney into the vascular tree, local renal tissue, or the lymphatic circulation due to tears in the fornices of the kidney from elevated intrarenal pressure which may occur during the lithotripsy procedure. Irrigant flow via the endoscope at high pressure accompanied by inadequate nephrostomy or ureteral drainage is responsible for these pressure spikes. The condition can be separated into three groups pyelovenous back flow, pyelosinus backflow, and pyelolymphatic backflow. Renal backflow commonly occurs at pressures>40 cm $H_2O$.

Thermoreversible hydrogel: Thermosensitive bio-adhesive hydrogel is synonymously referred to as thermoreversible hydrogel or RTgel. This hydrogel for use in the described methods is in liquid form at low temperatures and remain liquid in the process of administration to a patient (e.g., through instillation into the collecting system of the kidney or ureter). At elevated temperatures (e.g., typical human body temperature), thermoreversible hydrogel solidifies, thereby coating an internal body cavity. Low temperature can be defined less than 20° C., preferably less than 15° C. In a particular embodiment, low temperature can be less than 10° C. As used herein, a thermoreversible hydrogel is synonymous with a "thermosensitive bio-adhesive hydrogel", "reverse thermal hydrogel" (RTgel) and a "thermoreversible hydrogel." Particular examples of a thermoreversible hydrogel include compositions such as RTgel, which include a poloxamer with additional optional ingredients including HPMC and polyethylene glycol (PEG).

Wash: Use of a fluid to cleanse an area. In particular embodiments, the "wash" of an area results in a cleansing of the area. In particular embodiments of the described methods, a body cavity is "washed" after lithotripsy, which may and may not include the use of a ureteroscope/endoscopic brush to facilitate clearance of stone fragments entrapped within the thermosensitive bio-adhesive hydrogel. A "cold wash" may be used to liquify the thermosensitive bio-adhesive hydrogel and flush it and dust-like particles from the kidneys, ureters, bladder, and urethra.

II. Overview of Several Embodiments

Provided herein are methods for treatment of a nephrolithiasis in a subject, by administering to the subject a thermosensitive bio-adhesive hydrogel; and providing a lithotripsy procedure to the subject, wherein stone clearance rate is at least 90%, and wherein the thermo-reversible hydrogel comprises chitosan or at least one tri block copolymer having a general formula ABA or BAB copolymer, wherein A is a hydrophilic polymer block and B is a hydrophobic block polymer, thereby treating the nephrolithiasis.

In a particular embodiment, the thermosensitive bio-adhesive hydrogel protects the urothelium of the subject from internal thermal damage or disruption resultant from the lithotripsy procedure.

In some embodiments, the stone clearance is at least 90%-99.9%, inclusive.

In other embodiments, the method inhibits renal backflow, such as pyelovenous, pyelosinus, or pyelolymphatic backflow.

In particular embodiments, the lithotripsy procedure comprises exposing the patient to a high-power laser capable of reaching 200-500 watts.

In some embodiments, the lithotripsy procedure is ultrasonic lithotripsy, holmium laser lithotripsy (YAG), thulium fiber laser lithotripsy, super pulse thulium fiber laser lithotripsy, pneumatic, or electrohydraulic.

In a particular embodiment, the hydrogel partially or completely protects the urothelium from thermal damage. In yet a further embodiment, the hydrogel inhibits a peak intra-calyceal or intraureteral temperature of 38° C. during the lithotripsy procedure.

In other embodiments, the tri block copolymer having an ABA formula is EPO/PPO/EPO block copolymer. In a particular embodiment, the tri block copolymer having an ABA formula has an average molecular weight 1100-20000 Da inclusive. In yet a further embodiment, the tri block copolymer having ABA formula is Poloxamer 407 or Poloxamer 338.

In some embodiments, the hydrogel composition optionally further comprises a mucoadhesive polymer.

In other embodiments, the hydrogel composition has 15% (w/w)-40% (w/w) poloxamer 407 or Poloxamer 338 or any combination thereof, wherein the hydrogel further optionally includes 0.05% hydroxyl propylmethyl cellulose (HPMC).

In particular embodiments, the hydrogel is administered to the urothelium and inner lining of the kidney, ureter, bladder, and urethra.

In some embodiments, the hydrogel encapsulates the nephrolithiasis.

In particular embodiments, the lithotripsy further includes clearing stone fragments left in the hydrogel with a ureteroscope brush, sponge, suction, or other devices exclusive of stone baskets or pre-existing graspers.

In particular embodiments, the hydrogel includes about 27% or 30% Poloxamer 407. In yet a further embodiment, the hydrogel includes about 27% or 30% Poloxamer 338.

Additionally described herein are methods for protecting a subject from thermal damage or disruption during lithotripsy, by administering to the subject a thermosensitive bio-adhesive hydrogel; and providing a lithotripsy procedure to the subject, wherein the administration of the thermosensitive bio-adhesive hydrogel protects the subject from urothelium thermal damage associated with the lithotripsy, and wherein the thermo-reversible hydrogel comprises chitosan or at least one tri block copolymer having a general formula ABA or BAB copolymer, wherein A is a hydrophilic polymer block and B is a hydrophobic block polymer, thereby protecting the subject from thermal damage or disruption of the lithotripsy procedure.

Additionally described herein are methods for inhibition of nephrolithiasis regrowth in a subject, by administering to the subject a thermosensitive bio-adhesive hydrogel; and providing a lithotripsy procedure to the subject, wherein the administration of the thermosensitive bio-adhesive hydrogel encapsulates the renal stones and prevents displacement of renal stones during the lithotripsy procedure, and wherein the thermo-reversible hydrogel comprises chitosan or at least one tri block copolymer having a general formula ABA or BAB copolymer, wherein A is a hydrophilic polymer block and B is a hydrophobic block polymer, thereby inhibiting renal stone regrowth in a subject.

Further provided herein are methods for inhibiting renal backflow in a subject suffering from nephrolithiasis, by administering to the subject a thermosensitive bio-adhesive hydrogel; and providing a lithotripsy procedure to the subject, wherein the thermo-reversible hydrogel comprises chitosan or at least one tri block copolymer having a general formula ABA or BAB copolymer, wherein A is a hydrophilic polymer block and B is a hydrophobic block polymer, and wherein the renal backflow is selected from pyelovenous, pyelolymphatic and pyelosinus.

III. Treatment of Nephrolithiasis with a Thermosensitive Bio-Adhesive Hydrogel The challenge of treating nephrolithiasis is twofold: effective removal of the stones and fragments thereof, and protecting the subject from internal thermal damage or urothelial disruption caused by standard stone ablation methods which utilize a heat-producing methodology such as laser-mediated ablation. As demonstrated herein, application of a thermosensitive bio-adhesive hydrogel to the urothelium prior to stone ablation can provide an effective solution to this twofold challenge of treating nephrolithiasis.

Accordingly, described herein is a method for treatment of nephrolithiasis in a subject by administering to the subject a thermosensitive bio-adhesive hydrogel; and afterwards providing a lithotripsy procedure to the subject. Compositions comprising the noted thermosensitive bio-adhesive hydrogel for use in such methods are also described.

The described methods enable stone clearance of at least 90% and can protect a subject in need of such treatment from urothelial thermal damage and urothelial disruption associated with particular lithotripsy methods. The thermo-reversible hydrogel for use in these methods includes chitosan or at least one tri block copolymer having a general formula ABA or BAB copolymer, wherein A is a hydrophilic polymer block and B is a hydrophobic block polymer.

The described methods aim to more effectively treat nephrolithiasis, prevent and/or inhibit recurrence of nephrolithiasis due to uncleared stone fragments, and/or protect a subject from nephrolithiasis treatment-related urothelial thermal damage or disruption. Nephrolithiasis can be any condition involving renal calculi, nephroliths or kidney stones found in one or more areas in the urinary tract of a subject, including human and non-human veterinary subjects. Areas of the kidneys and urinary tract commonly affected by renal calculi, nephroliths or kidney stones include, but are not limited to the major calices, minor calices, renal pelvis, and one or both ureters.

Nephrolithiasis, most commonly referred to as a "renal stone" or "kidney stone" is a mineral deposit, which can be visible to the eye and range from 2-80 mm in diameter. Fragments smaller than 2 mm, are categorized as being too small to remove by standard basket techniques; smaller stone particles, known as dust, are characterized by being less than or equal 250μ. Renal stones are commonly composed of concretions of calcium, oxalate, phosphate, struvite, uric acid, and cystine.

The methods described herein can, in certain embodiments, also reduce the occurrence of or treat renal backflow. Renal backflow can be separated into three distinguishable conditions including pyelovenous, pyelosinus, and pyelolymphatic. "pyelovenous backflow" refers to retrograde movement of urine from the renal calyces into the renal venous system via a tear in the fornix which surrounds the renal papilla. This condition results from distal obstruction or injection of solutions into the renal collecting system at pressures exceeding 40 cm $H_2O$. It can be appreciated that the claimed method prevents pyelovenous, pyelolymphatic, and pylosinus backflow, by application of the thermosensitive bio-adhesive hydrogel to the renal cavity prior to stone ablation; administration of the thermosensitive bio-adhesive hydrogel results in filling the calyces and their associated infundibulae thereby, as it warms into a semisolid state, creating a plug blocking exposure of the delicate fornices of the renal calyces to the higher pressures that may be achieved during the treatment of a stone in the renal pelvis.

It will also be appreciated that renal stones may block the ureter, which can lead to kidney infection or urosepsis, sepsis originating from the urogenital tract. Additionally, pyelovenous and pyelolymphatic backflow may be a harbinger to urosepsis as any bacteria within the stone may then gain access to the vascular or lymphatic system. The described method coats the urothelium in order to encapsulate the renal stones for removal while simultaneously filling and plugging the infundibulae and the calyces. Accordingly, the described method will minimize residual stone fragments by entrapping them for easier removal while simultaneously protecting against renal backflow and the possibility of urosepsis.

Standard minimally invasive kidney stone ablation methods include percutaneous stone removal and ureteroscopy which are usually accompanied by lithotripsy which may be via rigid pneumatic or ultrasound devices or by flexible laser fibers delivering Holmium: YAG or thulium laser energy. Larger biological concretions require physical breakage (via lithotripsy) in order to be removed either via a percutaneous access to the kidney (</=10 mm diameter) or via a trans-ureteral approach (</=6 mm diameter). Lithotripsy by application of laser energy to the stone creates many fragments which are readily dispersed from the original location of the concretion. Such methods succeed in breakage of the concentration to fragments which on average are 1-2 mm in size. While some residual fragments</=2 mm may pass spontaneously from the kidney, there are other fragments</=2 mm that may remain even at 3 months post surgery. These fragments may form the nuclei for the formation of new concretions in as many as 40% of patients within several years of their initial procedure. Moreover, the shattering process may cause fragments to move into inaccessible areas of the kidney thus preventing their identification and removal. The described methods which administer reverse (hernial hydrogel to the location of the kidney stone in the urinary tract coat the stone such that when it is fragmented, the fragments remain entrapped in the gel thereby enabling removal of at least 90% of the stone mass, including fragments and particles 2 mm or less in size.

The lithotripsy procedures for use in the subject methods can be divided into two general categories, extracorporeal lithotripsy and intracorporeal lithotripsy. Extracorporeal lithotripsy describes a method where the energy needed is generated outside the body; while intracorporeal lithotripsy describes a method where the energy needed is generated inside the body.

Extracorporeal lithotripsy refers to a category of non-invasive lithotripsy, in which the energy source emanates from outside the patient's body, such as but not limited to, a lithotripter, and travels through the patient's body until reaching the concretion targeted for fragmentation in a process called extracorporeal shock wave lithotripsy (ESWL). Extracorporeal lithotripsy works best with stones of small diameter that are soft and situated such that the distance from the patient's flank to the stone is under 10 cm. Various lithotriptors and methods exist for generating high-intensity, focused shock waves for the fragmentation of kidney stones inside the subject. A lithotriptor generating a spark gap discharge in water has been used to generate a shock wave within an ellipsoidal reflector, which couples and focuses the shock wave to fragment kidney stones inside the subject, using fluoroscopic or ultrasonic imaging to target the stone. Lithotriptors also exist that use a coil, in the form of a spherical segment, to produce magnetically induced self-converging shock waves that can be directed at a stone within the subject using fluoroscopic or ultrasonic imaging. Lithotriptor may also include piezoelectric elements to produce focused high-intensity shock waves. The treatment of renal stones by extracorporeal lithotripsy apparatus additionally requires an ultrasound or fluoroscopic locating system, for correctly positioning the lithotripsy apparatus and the subject relative to each other so that the concretion, such as a kidney stone, is located in the focus of the shock waves. In particular embodiments, the location of the concretion through use of an ultrasound or fluoroscopic locating system is performed prior to administering the described reverse thermal hydrogel composition. In other embodiments, ultrasound or other imaging can be used both prior to and following administration of the hydrogel, to ensure proper placement and/or sufficient amounts of the hydrogel. Using the lithotripsy apparatus, the focused shock waves are then passed into the subject, and act on the renal stone to disintegrate it into fragments, which can be naturally eliminated, or in particular embodiments, can be embedded into the provided hydrogel and then washed from the target body cavity.

As noted, in particular embodiments, a locating system is also used to identify the position of the stone within the subject. Particular non-limiting examples of locating systems for use in the current methods include but are not limited to an x-ray system or an ultrasound system. A visual display is provided by the locating system which includes a mark identifying the concretion and an indicator for the position of the focus. Devices of this type are utilized, for example, for disintegrating kidney stones within the subject, while being non-invasive.

Intracorporeal lithotripsy is a minimally invasive form of lithotripsy. Intracorporeal lithotripsy, which uses an endoscopic probe that is positioned in proximity to the concretion. The energy required for fragmentation is transferred through the probe to the concretion and the treatment process is visualized during fragmentation. The mode of energy transfer varies and differs depending on the physiological presentation of the renal stone.

Particular examples of intracorporeal lithotripsy, all of which can be utilized in the described methods, are laser, ultrasonic, and ballistic (i.e. pneumatic) lithotripsy. These modalities may be used via a percutaneous approach through a nephrostomy tract or via natural orifice surgery via the ureter.

Laser lithotripsy employs a fiber that passes through the endoscope and is positioned directly onto or within 1 mm of the surface of the renal stone. When applied, the fiber transmits laser energy for breaking up the stone. Non-limiting examples of lasers used in laser lithotripsy and associated lithotripsy procedures are high-power holmium laser lithotripsy (HP-HLL), thulium fiber laser (TFL), or super pulse TFL. It can be appreciated that the instillation of the described hydrogel prior to the lithotripsy procedure allows for an increased application of the laser, such that a holmium laser may be set from 1-2 J at 10-20 Hz, and to achieve dusting the laser may be set at 0.5-1 J at 40-80 Hz. Regarding a thulium device the fragmentation settings would be similar to the holmium laser, but to achieve dusting, the settings could go up to 0.05 and 800 Hz up to 0.025 and 2000 Hz. Although laser lithotripsy can be effective, in many instances the subject can suffer from fragment migration into the various renal calyces during laser lithotripsy, which leads to inability to access the fragments or the development of fragments under 2 mm which cannot be removed using current stone basket technology. Stone remnants after the procedure lead to new stones or stone regrowth and the need for a repeat procedure in upwards of 40% of patients within 4 years of their initial treatment. The instillation of the described hydrogel prior to the lithotripsy procedure significantly reduces fragment migration, thereby effectively inhibiting renal stone regrowth due to residual fragments.

Ultrasonic lithotripsy uses an ultrasound probe which emits high-frequency ultrasonic energy that has a disruptive effect upon the concretion. Direct contact of the probe tip and stone is necessary for the effectiveness of ultrasonic lithotripsy. It is also equipped with aspiration so smaller fragments can be evacuated from the field during the lithotripsy procedure.

Ballistic or pneumatic lithotripsy is based on a pure mechanical hammer effect transmitted along a probe that requires a rigid straight ureteroscope. The stone is fragmented and the surgeon then needs to remove the fragments using current stone basket technology.

The high levels of energy required for extracorporeal lithotripsy to produce the required shock waves can be harmful to the adjacent tissues and therefore potentially dangerous for the subject. In addition, it is understood that intracorporeal lithotripsy is not without hazards to a subject as described. Almost all lithotriptors that are intended for destroying concretions by bringing mechanical energy of impact or shock wave can, in certain instances, result in mechanical damage to the surrounding tissue. Also, the laser energy may generate a significant amount of heat which requires a rapid flow of irrigant to cool the surrounding urothelium.

Pneumatic and ultrasonic lithotripsy can only be used with a rigid endoscope and thus are relegated solely to a percutaneous approach via a nephrostomy tract. On the other hand, both electrohydraulic lithotripsy (EHL) and laser lithotripsy can be delivered via a flexible endoscope and thus are amenable for use either percutaneously or via an ureteroscopic approach. However, EHL is an older method seldom used today. Presently the vast majority of flexible lithotripsy is performed using lasers. For ureteroscopy of renal stones (e.g., retrograde intrarenal surgery (RIRS)), a flexible ureteroscope is passed along the urethra and bladder, and up the ipsilateral ureter to the renal stone. If the stone is small (e.g., less than or equal to 4 mm), it may be caught with a stone retrieval basket device and removed whole from the ureter. If the stone is larger, the stone will need to be fragmented, which is usually accomplished using laser lithotripsy. In such embodiments, the reverse thermal hydrogel is administered to the subject prior to insertion of the ureteroscope via a retrograde catheter passed into the ureter prior to ureteroscopy. In other embodiments, the reverse thermal hydrogel is provided by a catheter that is threaded through the ureteroscope and thereby guided to the treatment area under endoscopic vision.

In some embodiments, the described methods involve basketing the stone fragments following the laser lithotripsy. Basketing stone fragments is commonly combined, with lithotripsy. The procedure entails inserting a thin wire into the ureter with a basket configuration at the tip to grasp the fragments of the lasered renal stone for removal.

In some embodiments the thermosensitive bio-adhesive hydrogel is infused into and coats the urothelium and inner lining of the kidney, simultaneously surrounding an intact stone prior to the laser fragmentation or trapping stone fragments resultant from laser lithotripsy. In the former iteration, the thermosensitive bio-adhesive hydrogel coats the stone and fills the renal pelvis and the finger-like projections of the infundibulae and their associated calyces. Although typically the reverse thermal hydrogel will be provided to a subject prior to lithotripsy procedures performed to break apart a renal stone, in other embodiments, the hydrogel is applied after a stone is broken, thereby also trapping stone fragments and particles to facilitate their removal.

As described herein, application of the thermosensitive bio-adhesive hydrogel provides protection to the urothelium from thermal damage resulting from the laser used in lithotripsy procedures, specifically the thulium laser. The described method enables near-complete removal of the renal stone (90% or greater), and therefore inhibits stone seeding and recurrence, while preventing high intra-calyceal temperatures during thulium laser lithotripsy which can damage urinary tract tissue, such that the peak intra-calyceal temperature in the urothelium does not exceed 36° C., 37° C., 38° C., or 39° C. Maintaining this temperature will effectively protect the subject from heat peaks that are commonly produced by the laser used during the laser lithotripsy procedures.

In particular embodiments, laser lithotripsy procedures can increase the temperature of surrounding tissue to 44° C. or higher, the threshold for thermal damage to the urothelium. Administering the reverse thermal hydrogel prior to the lithotripsy procedure can reduce the elevation in temperature by 1° C., 2° C., 3° C., 4° C., 5° C., 6, ° C., 7° C., 8° C. or even more, such that the temperature of the surrounding tissue is never raised above 40° C., thereby protecting the surrounding tissue from damage.

Administration of the thermosensitive bio-adhesive hydrogel at the outset of the procedure would also protect the delicate fornices of the kidney from being exposed to intrarenal pressures above 40 cm $H_2O$. This would protect the kidney from developing pyelovenous, pyelolymphatic and/or pyelosinus backflow. This in turn would help prevent development of urosepsis in the case of lithotripsy of stones harboring bacteria.

In a particular embodiment the thermosensitive bio-adhesive hydrogel is administered to the bladder, the upper urinary tract (including: the ureters, renal pelvis and calyces). In particular embodiments, the hydrogel is administered before a lithotripsy procedure is performed. In other embodiments, the hydrogel is administered after a lithotripsy is performed. The thermosensitive hydrogel can be administered to the desired body cavity, and particularly within the urinary tract, by any method known to the art. In particular embodiments, the thermosensitive hydrogel is administered by a catheter or through the working channel of an endoscope. In other embodiments, the thermosensitive hydrogel is administered by the common technique of intravesical instillation.

In one embodiment the described method includes stone dusting following administration of the thermosensitive bio-adhesive hydrogel. Dusting is performed with a low pulse energy and high pulse repetition rate to obtain dust that is considered capable of passing naturally from the urinary tract. However, basketing may still be necessary, even following a dusting procedure. Dusting aims to turn stone fragments into dust particles<250μ in size, such as sand which is 100-1000 microns. In some embodiments, the kidney stones are ablated to sand fragments of anywhere between 100-1000 microns. In particular embodiments, the stones are ablated to <100 microns. It will be appreciated that the described methods can more effectively clear smaller stone fragments, thereby inhibiting and/or preventing the seeding of new stones from uncleared dust.

The application of the thermosensitive bio-adhesive hydrogel as described herein enables encapsulation of stone fragments and dusted pieces resultant from stone ablation procedures. The method described herein provides stone clearance of at least 90%, 91%, 92%, 92.2.%, 93%, 94%, 95%, 96%, 97%, 98% 99%, 99.5%, to 99.99% of the total stone mass.

In further embodiments the treatment further comprises clearing stone fragments embedded in the thermosensitive bio-adhesive hydrogel through use of a commercially available ureteroscope/endoscopic brush. In yet further embodiments the brush removal of the stone fragments is optionally followed by a cold wash to liquify the gel and flush it and dust-like particles from the kidneys, ureters, bladder, and urethra.

It will be appreciated that the method described herein may be used to treat a pancreatic stone, gall stone, biliary stone, or any such similar bodily composite. The described method may also be used to remove other solid masses within the urinary tract, such as ureteral and bladder stones. In still further embodiments, administration of the reverse thermal hydrogel might be used to entrap a ureteral or renal tumor, thereby making it easier to biopsy or treat as it would be rendered immobile.

In a further embodiment, the described methods provide a high clearance rate of stone fragments and/or dust. In particular embodiments, the described hydrogel is provided to a subject such that it effectively surrounds and encapsulates the renal stone and accordingly any fragments thereof resultant from a lithotripsy procedure. Thus, the described method provides a manner for inhibition and/or prevention of stone regrowth, which commonly occurs due to dust or fragments that remain in the subject due to incomplete clearance and/or the dispersing of the renal stone fragments or dust during standard lithotripsy.

IV. Thermosensitive Bio-Adhesive Hydrogel

The thermosensitive bio-adhesive hydrogel for use in the described methods comprises chitosan or at least one tri block copolymer having a general formula ABA or BAB copolymer, wherein A is a hydrophilic block and B is a hydrophobic block.

In particular embodiments the tri block copolymer has an ABA formula of EPO/PPO/EPO block copolymer. In other embodiments the tri block copolymer has an ABA formula with an average molecular weight of 1100-20,000 Da, inclusive.

In some embodiments the tri block copolymer has an ABA formula of Poloxamer. In particular embodiments the Poloxamer is Poloxamer 407, Poloxamer 188, Poloxamer 124, Poloxamer 237, and Poloxamer 338. In a particular embodiment the Poloxamer is Poloxamer 338 or 407.

In some embodiments the thermosensitive bio-adhesive hydrogel composition also includes 0.1% (w/w) to 5% (w/w) mucoadhesive polymer. In particular embodiments the hydrogel composition includes 15% (w/w)-40% (w/w) poloxamer 407.

In some embodiments the thermosensitive bio-adhesive hydrogel composition also includes 0.1% (w/w) to 5% (w/w) mucoadhesive polymer. In particular embodiments the hydrogel composition includes 15% (w/w)-40% (w/w) poloxamer 338, particularly 30% poloxamer 338. In further embodiments the hydrogel optionally includes 0.05% hydroxyl propylmethyl cellulose (HPMC).

The thermosensitive bio-adhesive hydrogel composition for use in the described methods includes a tri block copolymer having a general formulae ABA or BAB copolymer, wherein A is a hydrophilic block and B is a hydrophobic block. More specifically, A or B is selected from PEO ((Poly(ethylene oxide)), PLGA (poly(lactic-co-glycolic) acid, PLA (polylactic acid) and PPO (polypropylene oxide) PGA (Poly Glycolic Acid), PCL—(Polycaprolactonn), PCLA—Poly(ε-caprolactone-co-lactide), PCBCL—poly(α-carboxylate-co-α-benzylcarboxylate-ε-caprolactone), or includes at least two cyclic monomers selected from the group consisting of glycolide, lactide, e-caprolactone, p-dioxanone (1,4-dioxan-2-one), trimethylene carbonate (1,3-dioxan-2-one); 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; chi-diethylpropiolactone; ethylene carbonate; ethylene oxalate; 3-methyl-1,4-dioxane-2,5 dione; 3,3-diethyl-1,4-dioxan-2,5-dione, 6,8 dioxabicycloctane-7-one; beta-propiolactone; gama-butyrolactone,delta-valerolactone; epsilon-decalactone, 3-methyl-1,4-dioxane-2,5dione; 1,4-dioxane-2,5-dione; 2,5-diketomorpholine, alpha,alpha-diethylpropiolactone, gama-butyrolactone; 1,4-dioxepan-2-one,1,5-dioxepan-2-one; 6,6-dimethyl-dioxepan-2-one; 6,6-dioxabicycloctane-7-one; or 5,5-dimethyl-1,3-dioxan-2-one.

In particular embodiments the thermosensitive bio-adhesive hydrogel composition includes a tri block copolymer having a formula of PEO/PPO/PEO and has an average molecular weight in the range of 1100-20,000 Da.

In particular embodiments, the thermosensitive bio-adhesive hydrogel composition includes a poloxamer or combination of different poloxamers such as but not limited to Poloxamer 407, Poloxamer 188, Poloxamer 338 and Poloxamer 68.

In particular embodiments the gel component of the thermosensitive bio-adhesive hydrogel compositions is present in concentrations of 5%-45% (w/w) and ranges therein, such as 10%-35%, 20%-45%, 15%-35%, 20%-40%, 20%-35%. In another particular embodiment, the gel component is present in a concentration of 24%, 27%, 28%, 29%, 30%, 31%, or 32%.

In a particular embodiment, the thermosensitive bio-adhesive hydrogel composition includes 5% to 45% (w/w), and any range therein, of a PEO/PPO block copolymer and also includes at least one of a mucoadhesive enhancing agents, dissolution rate controlling agent, gelation temperature controlling agent, pH controlling agent, absorption enhancer/tight junction modifier/cell membrane permeability enhancer, organic acid or cyclodextrins. In some embodiments the thermosensitive bio-adhesive hydrogel optionally includes an anesthetic, such as but not limited to lidocaine.

In particular embodiments, the mucoadhesive enhancing agent can optionally include, but is not limited to, HPMC (hydroxyl propylmethyl cellulose), agarose, chitosan, gelatin, hyaluronic acid, carrageenan, pectin, sodium alginate, polyacrylic acids, polymers based on poly(meth)acrylic acid, carbopol, polycarbophil, polyacrylic acid, polyacrylates, copolymer of acrylic acid and polyethylene glycol, copolymer of methylvinyl ether and methacrylic acid, poly-2-hydroxyethylmethacrylate, copolymer of acrylic acid and ethylhexylacrylate, cellulose derivatives (for example methylcellulose (MC), hydroxy-propylcellulose (HPC), hydroxy ethyl cellulose, thiolated CMC other hydroxyalkylcelluloses and hydroxyalkylmethylcelluloses, carboxy-methylcelluloses (CMC), Polyvinylpyrrolidone (PVP) and its copolymers (N-vinyl-2-pyrrolidone), Poly-N-2-hydroxypropylmethacrylamide, polyhydroxyethylene, polyvinyl alcohol (PVA), and thiolated polymers.

In particular embodiments, dissolution rate controlling agents can include, but are not limited to, silicon dioxide or any derivatives thereof, nanoparticles or microparticles of Poly (Lactide-co-Glycolide) (PLGA), polylactic acid (PLA), Polyglycolic acid (PGA), PLA-PEG or PLGA-PEG copolymers, nanoparticles or microparticles polystyrene or polymethyl methacrylate (PMMA), calcium carbonate, microcrystalline cellulose, aluminum hydroxide, Eudragit® NE, Eudragit® RS and RL, cellulose acetate and cellulose acetate butyrate, crospovidones, crosslinked sodium carboxymethylcellulose, crosslinked sodium carboxymethylstarch, thickening agents, soy, iodinated aromatic compounds, cyclodextrin, and cholesterol.

In particular embodiments, gelation temperature controlling agents include, but are not limited to, urea, polyethylene glycol, short chain fatty acid and their salts (sodium octanoate, sodium dodecyl sulfate), ethanol, Glyceryl monostreatrate, Isopropyl myristate, and Polysorbate surfactants.

In some embodiments, tight junction modifier/cell membrane permeability enhancers include, but are not limited to, anionic surfactants, non-anionic surfactants, charged polymers, dimethyl sulfoxide (DMSO), decylmethyl sulfoxide, tert-butyl cyclohexanol, fatty acids their esters and salts, ethanol, nicotinamide, urea, perfluoropolyether, monoterpene ketones, disodium citrate, succinic acid, alkyl saccharides, hyaluronidase, and tris.

In some embodiments pH modifying substances include: group consisting of acids, bases and buffer substances, adipic acid, malic acid, lactic acid, ascorbic acid, aspartic acid, benzenesulfonic acid, benzoic acid, succinic acid, citric acid, ethanesulfonic acid, 2-hydroxyethanesulfonic acid, fumaric acid, gluconic acid, glucuronic acid, glutamic acid, potassium hydrogentartrate, maleic acid, malonic acid, methanesulfonic acid, toluenesulfonic acid, trometamol, tartaric acid, Tris-HCl, NaOH, sodium caprylate phosphate buffer.

In another embodiment, the thermosensitive bio-adhesive hydrogel includes between 10% and 45% (w/w) Poloxamer or mixture of different poloxamers and between 0.05% and 0.5% (w/w) mucoadhesive agent.

In other embodiments the thermosensitive bio-adhesive hydrogel includes between 10% and 35% (w/w) EPO/PPO block copolymer and between 0.1% and 5% (w/w) mucoadhesive agent.

In a particular embodiment, the thermosensitive bio-adhesive hydrogel comprises 27% Poloxamer 407, and optionally 0.05%-0.2% HPMC and/or 1% PEG 400.

In some embodiments the hydrogel comprises about 30% Poloxamer 407. In further embodiments the hydrogel comprises about 30% Poloxamer 338.

The following examples are provided to illustrate certain particular features and/or embodiments. These examples should not be construed to limit the disclosure to the particular features or embodiments described.

EXAMPLES

Example 1: Intrarenal Gel for Stone Fragment Containment and Extraction During Endoscopic Procedures In prior in-vitro studies from our laboratory, we have demonstrated the functionality of RTGel (UroGen Pharma, NY), for creating a clear, tenacious "stone clot" which could then be extracted, along with embedded stone fragments, with conventional stone baskets. We evaluated different formulations of gel (e.g., formulations that include 30% poloxamer 338+0.05% HPMC in water for instillation, 16%-30% poloxamer 407, or 20%-30% poloxamer 308 with and without PEG400 in water for instillation) with varying gelation temperatures with regard to time to solidification, the tenacity of stone entrapment, and optimal removal techniques. We then evaluated the efficacy and efficiency of the gel, in an ex vivo porcine kidney. In this study, we noted that when the gel was infused around the intact stone, the stone remained more stationary allowing for more efficient laser fragmentation, entrapment of fragments and more efficient stone extraction using an endoscopic FDA approved brush, as the bristles readily engaged the stone containing gel thereby facilitating extraction. With this approach, we achieved a 92% stone clearance in our laboratory studies. This is dramatically improved compared to conventional techniques which in clinical practice only achieve 50-60% renal stone clearance, in the most experienced hands.

Methods

Canine calcium oxalate stones were acquired and their volume, dimensions, mass, and density in Hounsfield units were measured. Two pigs (4 renal units) were studied; the right kidney was randomized to either the experimental kidney (use of thermosensitive bio-adhesive hydrogel+) or the control kidney (no thermosensitive bio-adhesive hydrogel−). The contralateral kidney was assigned the remaining option.

Experimental Kidney

A midline laparotomy incision was made, and the previously randomized experimental kidney was exposed. The renal pelvis was identified, exposed, incised with scissors, and the previously prepared canine stone was implanted. A temperature probe was also placed alongside the stone. The pyelotomy was then closed with a 3-0 Vicryl suture creating a water-tight seal. The laparotomy was closed with skin staples. A 35 cm, 16F ureteral access sheath was passed retrograde into the ureter over an 0.035 Amplatz superstiff guidewire until it resided in the ureteropelvic junction. Proper placement was confirmed with fluoroscopy. A 5 Fr angled Kumpe catheter was passed through the sheath under direct visualization to the location of the stone in the renal pelvis. 5 cc of thermosensitive bio-adhesive hydrogel was then injected into the area through the Kumpe catheter using a high-pressure injector. The Kumpe catheter was then removed. Retrograde ureteroscopy was then performed. Superpulse thulium fiber (sTFL) laser lithotripsy was performed via a Storz video flexible ureteroscope utilizing a 200-micron fiber at dusting settings (0.2 J and 80 Hz). The stone within the thermosensitive bio-adhesive hydrogel (e.g., gel including 30% poloxamer) was ablated with the goal of creating fragments≤100 microns (i.e., dust). Once the stone was sufficiently treated, the laser fiber was removed and larger fragments were basketed, extracted, and their weights recorded. Then the ureteroscopic endoscopic brush (Karl Storz ureteroscope) was passed and any remaining pieces of stone embedded within the gel were swept and removed. Finally, cold saline irrigation was instilled to liquify the gel and wash it out of the system.

Control Kidney

A midline laparotomy incision was made, and the previously randomized control kidney was exposed. The renal pelvis was identified, exposed, incised with scissors, and the previously prepared canine stone was implanted. A temperature probe was also placed alongside the stone. The pyelotomy was then closed with a 3-0 vicryl suture creating a water-tight seal. The laparotomy was closed with skin staples. A 35 cm, 16F ureteral access sheath was passed retrograde over an 0.035 Amplatz superstiff guidewire until it resided in the ureteropelvic junction. Proper placement was confirmed with fluoroscopy. Retrograde ureteroscopy was then performed. The stone was then dusted with the sTFL laser using pre-set dusting settings (0.2 J and 80 Hz—16 watts) with the goal of creating fragments<100 microns. These fragments were then basketed, extracted, and their weights recorded.

At the conclusion of the experiment, the animal was euthanized, both kidneys were harvested, and the renal pelvis was opened on the benchtop. All remaining fragments were drained and sequentially sieved to measure the size of the remaining fragments. This collection of stones was dried and weighed for further analysis.

Results

The RTgel (comprising 30% poloxamer 338 and 0.05% HPMC in water for instillation) used herein was found to have the needed tenacity to hold the fragments within the gel both during the fragmentation process and during the extraction process.

The four canine calcium oxalate stones, preimplantation, were of similar size and composition, with an average dry mass of 737.5 mg, volume of 0.5 mL, diameter of 11.8 mm, and density of 1331.0 Hounsfield units. A mean of 755.5 mg of fragments were retrieved in the experimental thermosensitive bio-adhesive hydrogel group, compared to a mean of 657.4 mg in the control group. Further, a mean of 5.45 mg of fragments remained in the kidney after extraction in the experimental group (thermosensitive bio-adhesive hydrogel+) compared to 56.95 mg in the control group. Thus, in the experimental kidneys treated with the thermosensitive bio-adhesive hydrogel, 99.3% of stone fragments by mass were cleared compared to 92.2% in control kidneys. Finally, the average time for completion of the procedure with the thermosensitive bio-adhesive hydrogel was 73 minutes compared to 81 minutes without the thermosensitive bio-adhesive hydrogel. Results from this study are summarized in Table 1. As such, with the hydrogel the procedure was both more effective (higher stone clearance) and more efficient (less time expended). In addition, peak intra-calyceal temperature without Hydrogel was 55° C. and the control kidney temperature exceeded 44° C. four times during lithotripsy. In contrast, in the experimental kidneys with hydrogel formulations as described herein, the peak intracalyceal temperature was 36° C.

TABLE 1

|  | Experimental | Control |
|---|---|---|
| Starting Stone Mass (mg) | 761 | 714 |
| Mass Retrieved (mg) | 755.5 | 657.4 |
| Mass Remaining in Kidney (mg) | 5.5 | 56.6 |
| Percent Mass Cleared (%) | 99.3 | 92.2 |
| Procedure Time (minutes) | 73 | 80.5 |
| Peak Intra calyceal Temperature (° C.) | 36 | 55 |
| Times Peak Temperature Exceeded 44° C. | 0 | 4 |

CONCLUSIONS

The described method provides a superior method of stone clearance, and fragments thereof. The use of the thermosensitive bio-adhesive hydrogel reduced the length of surgery and could be completely washed out of both kidneys. Moreover, this study employed the thulium fiber laser, which more effectively dusts stones than the currently used holmium laser; this attribute of the sTFL may have also contributed to the high clearance rate in both groups. In addition, the stone was treated more rapidly when the hydrogel was used.

Also, the application of the thermosensitive bio-adhesive hydrogel allows for insulation of the urothelium and inner lining of the kidney, thereby potentially protecting it from the heat generated during the lithotripsy procedure, by preventing high intra-calyceal temperatures during TFL.

Furthermore, the gel may protect the kidney from renal pyelo-venous backflow, which can in turn, decrease the risk of urosepsis. The high viscosity of the thermosensitive bio-adhesive hydrogel employed is a unique property that facilitates this insulation and protection by filling the infundibulae and calyces. The thermal insulation may be even more critical in the ureter given the thin wall and tenuous blood supply of the ureter and the very confined space in which the laser is being activated. The ureter is prone to stricture formation should thermal injury occur. The results of ureteral stricture can lead to corrective surgery or even result in loss of the kidney. The described hydrogel has the ability to protect the ureter from high temperature spikes during laser lithotripsy which was shown in a different study. Of note, the Canadian Drug Administration has issued a black box warning with regard to using the sTFL in the ureter due to concerns over postoperative ureteral stricture formation. Accordingly, the methods described herein could be used to prevent such postoperative complications.

Finally, provision of the described hydrogel around the stone effectively trapped any fragments that would normally escape into adjacent calyces behind the stone during fragmentation, a common place for residual fragments to reside to. Thus, when exploring the kidney to identify any residual fragments, the calyces behind the stone were clear of any fragments as the gel precluded their entry.

The use of varied gel compositions in lithotripsy has been previously proposed (U.S. Pat. Nos. 9,925,311, 8,372,037;

International Pat. Pub. No. WO 2005/037062). However, none of these proposals have demonstrated the improved stone clearance, more efficient stone clearance, avoidance of temperature spikes, potential to preclude renal backflow, and inhibition of stone regrowth, as described herein which is a direct consequence of the gel formulation used in this example. Moreover, none of these proposals provide a gel formulation to encapsulate a target stone such that upon lithotripsy directly to the gel-encapsulated stone, stone fragments, including dust, are captured within the gel.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treatment of a nephrolithiasis in a subject, the method comprising:
   administering to the subject a thermo-reversible hydrogel into the subject's renal pelvis to encapsulate the nephrolithiasis; and
   providing a lithotripsy procedure to the subject,
   wherein stone clearance rate is at least 94%, and
   wherein the thermo-reversible hydrogel comprises chitosan or at least one tri block copolymer having a general formula ABA or BAB copolymer, wherein A is a hydrophilic polymer block and B is a hydrophobic block polymer,
   thereby treating the nephrolithiasis.

2. The method of claim 1, wherein the thermosensitive thermo-reversible hydrogel protects urothelium of the subject from internal thermal damage or disruption resultant from the lithotripsy procedure.

3. The method of claim 2, wherein the hydrogel partially or completely protects the urothelium from thermal damage.

4. The method of claim 3, wherein the hydrogel inhibits peak intra-calyceal or intraureteral temperature of 38° C. during the lithotripsy procedure.

5. The method of claim 1, wherein the stone clearance is at least 99%.

6. The method of claim 1, wherein the method inhibits a renal backflow selected from the group consisting of pyelovenous, pyelosinus, and pyelolymphatic backflow.

7. The method of claim 1, wherein the lithotripsy procedure comprises exposing the patient to a high-power laser capable of reaching 200-500 watts.

8. The method of claim 1, wherein the lithotripsy is selected from the group consisting of ultrasonic lithotripsy, holmium laser lithotripsy (YAG), thulium fiber laser lithotripsy, super pulse thulium fiber laser lithotripsy, pneumatic, and electrohydraulic.

9. The method of claim 1, wherein the tri block copolymer having an ABA formula is EPO/PPO/EPO block copolymer.

10. The method of claim 9, wherein the tri block copolymer having an ABA formula has an average molecular weight 1100-20000 Da inclusive.

11. The method of claim 1, wherein the tri block copolymer having ABA formula is Poloxamer 407 or Poloxamer 338.

12. The method of claim 1, wherein the hydrogel composition further comprises a mucoadhesive polymer.

13. The method of claim 1, wherein the hydrogel composition comprises 15% (w/w)— 40% (w/w) poloxamer 407 or Poloxamer 338 or any combination thereof, wherein the hydrogel further optionally includes 0.05% hydroxyl propylmethyl cellulose (HPMC).

14. The method of claim 1, wherein the hydrogel encapsulates the nephrolithiasis.

15. The method of claim 1, wherein the lithotripsy further comprises clearing stone fragments left in the hydrogel with a ureteroscope brush, sponge, suction, or other device exclusive of stone baskets or pre-existing graspers.

16. The method of claim 1, wherein the hydrogel comprises about 27% or 30% Poloxamer 407.

17. The method of claim 1, wherein the hydrogel comprises about 27% or 30% Poloxamer 338.

18. The method of claim 1, wherein an intrarenal pressure does not rise above 40 cm $H_2O$.

19. A method for protecting a subject from thermal damage or disruption during lithotripsy, the method comprising:
   administering to the subject a thermosensitive bio-adhesive hydrogel; and
   providing a lithotripsy procedure to the subject,
   wherein the administration of the thermosensitive bio-adhesive hydrogel protects the subject from urothelium thermal damage associated with the lithotripsy, and
   wherein the thermo-reversible hydrogel comprises chitosan or at least one tri block copolymer having a general formula ABA or BAB copolymer, wherein A is a hydrophilic polymer block and B is a hydrophobic block polymer,
   thereby protecting the subject from thermal damage or disruption of the lithotripsy procedure.

20. A method for inhibition of nephrolithiasis regrowth in a subject, comprising:
   administering to the subject a thermosensitive bio-adhesive hydrogel; and
   providing a lithotripsy procedure to the subject,
   wherein the administration of the thermosensitive bio-adhesive hydrogel encapsulates the renal stones and prevents displacement of renal stones during the lithotripsy procedure, and
   wherein the thermo-reversible hydrogel comprises chitosan or at least one tri block copolymer having a general formula ABA or BAB copolymer, wherein A is a hydrophilic polymer block and B is a hydrophobic block polymer,
   thereby inhibiting renal stone regrowth in a subject.

* * * * *